United States Patent [19]

Suzuki et al.

[11] Patent Number: 5,405,996
[45] Date of Patent: Apr. 11, 1995

[54] PROCESS FOR PRODUCING ACETIC ACID

[75] Inventors: Toshiro Suzuki; Hiroko Yoshikawa; Kenichi Abe; Kenichi Sano, all of Oita, Japan

[73] Assignee: Showa Denko K.K., Tokyo, Japan

[21] Appl. No.: 225,458

[22] Filed: Apr. 6, 1994

[30] Foreign Application Priority Data

Apr. 6, 1993 [JP] Japan .................................. 5-079730
Jun. 11, 1993 [JP] Japan .................................. 5-140910

[51] Int. Cl.⁶ .............................................. C07C 51/16
[52] U.S. Cl. ................................... 562/548; 502/262; 502/313; 502/339
[58] Field of Search ............... 562/548, 536; 502/210, 502/262, 313, 317, 337, 338, 339

[56] References Cited

U.S. PATENT DOCUMENTS

| | | | |
|---|---|---|---|
| 4,935,549 | 6/1990 | Kamiguchi et al. | 562/548 |
| 5,162,578 | 11/1992 | McCain, Jr. et al. | 562/512.2 |
| 5,330,955 | 7/1994 | Wegman | 502/210 |

FOREIGN PATENT DOCUMENTS

| | | | |
|---|---|---|---|
| 0156498 | 10/1985 | European Pat. Off. | |
| 47-13221 | 7/1972 | Japan | 16/B612 |
| 51-29425 | 3/1976 | Japan | 16/B612 |
| 54-57488 | 5/1979 | Japan | B01J 23/44 |
| 1025679 | 1/1978 | United Kingdom. | |
| 1508331 | 4/1978 | United Kingdom. | |

Primary Examiner—Arthur C. Prescott
Attorney, Agent, or Firm—Sughrue, Mion, Zinn, Macpeak & Seas

[57] ABSTRACT

A process for producing acetic acid comprising reacting ethylene and oxygen in the presence of a catalyst comprising metallic Pd and at least one member selected from the group consisting of heteropoly-acids and their salts, or in the presence of a catalyst comprising metallic Pd, at least one member selected from the group consisting of heteropoly-acids and their salts and at least one member selected from the group consisting of metallic elements of Groups 11, 14, 15 and 16 of the Long-Form Periodic Table.

33 Claims, No Drawings

PROCESS FOR PRODUCING ACETIC ACID

BACKGROUND OF THE INVENTION

1. Field of the Invention

The present invention relates to a process for producing acetic acid from ethylene and oxygen by one-stage catalytic reaction.

2. Description of the Related Art

Acetic acid has heretofore been practically produced by a process comprising oxidizing acetaldehyde, a process comprising reacting methanol with carbon monoxide and a process comprising oxidizing lower paraffin and the like.

The process comprising oxidizing acetaldehyde is a process of two-stage oxidation, namely, oxidation of ethylene to form acetaldehyde and oxidation thereof to form acetic acid. Since the Pd ion Contributing to oxidation of ethylene in this process cannot oxidize acetaldehyde thus produced, the catalysts used in the two stages differ from each other. Direct synthesis of acetic acid by this process is therefore difficult. The process comprising carbonylation of methanol has a disadvantage that the cost of Rhodium, the catalyst used in this process, is extremely high. On the other hand, the process comprising oxidizing lower hydrocarbon synthesizes acetic acid by one stage. However, the reaction conditions are comparatively strict, and as a result many by-products are formed. Accordingly, the process has problems of improving the reaction selectivity and the yield. Furthermore, the processes mentioned above are all carried out by liquid phase homogeneous reactions, and therefore require complicated operations to recover catalysts, separate products, and perform other procedures.

Many catalysts have been proposed for processes of producing acetic acid from ethylene by one-stage oxidation. For example, there is a disclosure of a process wherein Pd metal-phosphoric acid or a sulfur-containing catalyst modifying agent is used (Japanese Unexamined Patent Publication (Kokai) Nos. 47-13221 and 51-29425). Moreover, there is a disclosure of a process in which the use of a catalyst, a Pd salt of a certain type of heteropoly-acid, is effective (Japanese Unexamined Patent Publication (Kokai) No. 54-57488). It is particularly industrially important in carrying out reactions using these catalysts to enhance the activity thereof, reduce the deterioration of age thereof as much as possible, and use catalysts exhibiting good selectivity of acetic acid. However, it is difficult to conclude that those catalysts which have heretofore been proposed exhibit satisfactory properties when used in the production of acetic acid on a industrial scale.

Further, there is proposed a gas phase one stage oxidation process in which a catalyst consisting of a three-component oxygen compound prepared by using a heteropoly-acid is used (Japanese Examined Patent Publication (Kokoku) No. 46-6763). The heteropoly-acid is used as a source for providing elements necessary for forming the three-component oxygen compound and, thus, is converted thereto as a result of sintering during the preparation process of the catalyst.

SUMMARY OF THE INVENTION

An object of the present invention is to provide a process for industrially advantageously producing acetic acid by reaction of ethylene and oxygen.

For the purpose of achieving the object as described above, the present inventors have carried out intensive research on enhancing the performance of catalysts used during the production of acetic acid from ethylene and oxygen. As a result, the present inventors have discovered a catalyst as described below which exhibits an extremely high space time yield and a low selectivity of carbon dioxide and has an extended life, and have thus completed the present invention.

Accordingly, the present invention provides a process for producing acetic acid comprising reacting ethylene and oxygen in the presence of a catalyst comprising (a) metallic Pd and (b) at least one member selected from the group consisting of heteropoly-acids and their salts.

The present invention also provides a process for producing acetic acid comprising reacting ethylene, and oxygen in the presence of a catalyst comprising (a) metallic Pd, (b) at least one member selected from the group consisting of heteropoly-acids and their salts and (c) at least one member selected from the group consisting of metallic elements of Groups 11(1B), 14(4B), 15(5B) and 16(6B) of the Long-Form Periodic Table.

DESCRIPTION OF THE PREFERRED EMBODIMENTS

In the present invention, the heteropoly-acids and their salts may be used alone or as a combination of two or more thereof. The heteropoly-acids may contain one hetero-atom and one or more poly-atoms. The hetero-atom may preferably be selected from the group consisting of phosphorus, silicon, boron, aluminum, germanium, titanium, zirconium, cerium, cobalt, chromium and sulfur, and the poly-atoms may preferably be selected from the group consisting of molybdenum, tungsten, vanadium, niobium and tantalum.

Examples of the heteropoly-acids may include silicotungstic acid, phosphotungstic acid, phosphomolybdic acid, silicomolybdic acid, tungstomolybdophosphoric acid, tungstomolybdosilisic acid, tungstovanadophosphoric acid tungstovanadosilisic acid, molybdovanadophosphoric acid, molybdovanadosilisic acid, berotungstic acid, boromolybdic acid, tungstomolybdoboric acid, molybdoaluminic acid, tungstoaluminic acid, molybdotungstoaluminic acid, molybdogermanic acid, tungstogermanic acid, molybdotungstogermanic acid, molybdotitanic acid, tugnstotitanic acid, molybdotungstotitanic acid, cericmolybdic acid, cerictungstic acid, cericmolybdotungstic acid, molybdocobalt acid, tungstocobalt acid, molybdotungstocobalt acid, phosphoniobic acid, siliconiobic acid and silicotantalic acid. Among them, silicotungstic acid, phosphotungstic acid, phosphomolybdic acid, silicomolybdic acid, tungstomolybdophosphoric acid, tungstomolybdosilisic acid, tungstovanadophosphoric acid, tungstovanadosilisic acid, molybdovanadosilisic acid, borotungstic acid, boromolybdic acid and boromolybdotungstic acid are especially preferred.

The salts of heteropoly-acids may be metal or onium salts in which the hydrogen atoms or an acid formed by condensing two or more inorganic oxygen acid are partially or entirely substituted by one or more metal or onium cations. The metals by which the hydrogen atoms of the heteropoly-acids are substituted are selected from the group consisting of the metals of the Groups 1(1A), 2(2A), 11(1B) and 13(3B) of the Long-Form Periodic Table such as alkali metals, alkaline earth metals, copper, silver, gold, aluminum, gallium, indium and thallium. As examples of the onium salts, there may be mentioned ammonium salts derived from ammonia or an amine. Among the heteropoly-acid salts, lithium, sodium, potassium, cesium, magnesium, barium, copper, gold and galliume salts are especially preferred, with the most preferred examples being lithium, sodium and copper salts of phosphotungstic acid and lithium, sodium and copper salts of silicotungstic acid.

In the catalyst used in the first aspect of the present invention, the proportion of the components (a):(b) may preferably be 1 g atom: 0.025 to 500 g molecules, especially 1 g atom: 0.1 to 400 g molecules. Where the amount of the component (b) is less than 0.025 g molecule per g atom or Pd, the combustion reaction of ethylene may be markedly increased. On the other hand, where the amount of the component (b) is more than 500 g molecules, the acetic acid-formation activity may be reduced.

The catalyst is useful as a substance comprising only the components (a) and (b), but is advantageously used in the state of being supported on a carrier.

In the catalyst, Pd exists on the carrier not as a Pd salt of a heteropoly-acid but as Pd metal, and the heteropoly-acid or its salt is considered to exist in the vicinity thereof. As a result, the mutual action of Pd metal and the heteropoly-acid or its salt makes the catalyst extremely active and selective, and the catalyst exhibits excellent acetic acid-formation activity and selectivity at a low temperature compared with a palladium salt of a heteropoly-acid (Japanese Unexamined Patent Publication (Kokai) No. 54-57488) or with a three component polladium-containing oxygen compound (Japanese Examined Patent Publication (Kokoku) No. 46-6763).

Pd metal may be supported by a conventional method. For example, a catalyst carrier is immersed in a solution of a soluble salt such as palladium chloride, sodium tetrachloropalladate (II), palladium nitrate, palladium sulfate and palladium acetate and dried, and the palladium compound is reduced to metal with a suitable reducing agent such as hydrogen and hydrazine. A palladium salt may also be reacted with an alkali to form a corresponding palladium oxide or palladium hydroxide, which is then reduced to Pd metal. The alkali salt is removed by washing with water after reduction. Usually the amount of Pd to be supported is preferably 0.01 to 6% by weight, more preferably 0.1 to 2% by weight based on the weight of the carrier. The use of Pd in an amount of more than 6% by weight is economically inadvantageous. There is no specific limitation on the method for supporting Pd and the heteropoly-acid or its salt on the carrier. However, usually it is advantageous to support Pd at first. Pd metal and the heteropoly-acid may be precipitated or deposited on the carrier by any freely determined method.

Any of porous substances or substances capable of being made porous by granulation which are generally used as carriers may be used as a carrier substance in the present invention. Example of the carrier substance are silica, diatomaceous earth, montmorillonite, titania, activated carbon, alumina and silica alumina.

Any of methods such as an impregnation method, a method of evaporation to dryness, a kneading-molding method and an adhering method may be applied to the method for supporting the heteropoly-acid in the present invention. However, it is not preferable to heat treat the catalyst at a temperature exceeding approximately 350° C. after supporting the heteropoly-acid because the heating causes destruction of the heteropoly-acid skeleton and as a result deteriorates the acetic acid-formation activity and selectivity of the catalyst.

In the catalyst used in the second aspect of the present invention, the component (c) may preferably selected from copper, silver, tin, lead, antimony, bismuth, selenium and tellurium. The metallic element of the component (c) may be contained as a metal or a compound of the element.

The proportion of the components (a):(b):(c) may preferably be 1 g atom: 0,025 to 500 g molecules: 0.005 to 10 g atoms, more preferably 1 g atom: 0.1 to 400 g molecules; 0.01 to 5 g atoms. Where the amount of the component (b) is less than 0.025 g molecule per g atom of Pd, the combustion reaction of ethylene may be markedly increased. On the other hand, where the amount of the component (b) is more than 500 g molecules, the acetic acid-formation activity may be reduced.

Most preferably, the catalyst comprises of three components of (a') metallic Pd, (b') at least one member selected from the group consisting of lithium, sodium and copper salts of phosphotungstic acid and lithium, sodium and copper salts of silicotungstic acid and (c') at least one member selected from the group consisting of bismuth, selenium and tellurium.

The catalyst is useful as a substance comprising only the components (a), (b) and (c), but is advantageously used in the state of being supported on a carrier.

In the catalyst, Pd exists not as a Pd salt of the heteropoly-acid but as Pd metal, and the heteropolyacid, its salt or the component (c) is considered to exist in the vicinity thereof. As a result, the mutual action of metal Pd and the heteropoly-acid, its salt or the component (c) makes the catalyst realize extremely high activity and selectivity, and the catalyst exhibits excellent acetic acid-formation activity and selectivity at a low temperature compared with a palladium salt of a heteropoly-acid in the prior art (Japanese Unexamined Patent Publication (Kokai) No. 54-57488) and with a three component palladium-containing oxygen compound (Japanese Examined Patent Publication (Kokoku) No. 46-6763).

There is no specific limitation on the method for preparing the catalyst, and a known method for supporting a metal catalyst on a carrier may suitably be utilized. It may be appropriate to prepare the catalyst by supporting on a suitable carrier a suitable palladium compound and at least one compound of a metal or metals selected from the metals of the component (c), reducing the compound or compounds by a known suitable method, and supporting at least one compound selected from heteropoly-acids and their salts.

For example, the catalyst may be prepared as follows: a Pd compound and a compound or compounds of at least one metal selected from the metals of the component (c) are dissolved in a suitable solvent; a carrier is placed in the resultant solution; the above-mentioned components are allowed to adhere thereto by drying the solution, or precipitated thereon by adding a precipitating medium such as an alkali in the solution; the adhering or precipitated components are reduced by a suitable reducing agent such as hydrogen or hydrazine; and at least one compound selected from heteropoly-acids and their acid salts is supported.

There is no specific limitation on the order of supporting on a carrier the components (a), (b), and (c). These substances may be supported thereon simultaneously, or successively.

The component (c) is supported not as heteropoly-acid salts, but they are supported separately from the heteropoly-acids and their salts.

A method such as an impregnation method, a method of evaporation to dryness and an adhering method are suitably applied to the method for supporting the heteropoly-acid.

There is no particular limitation on the Pd compound used for the preparation of the catalyst. Typical examples of the Pd compound are halides such as palladium chloride, organic acid salts such as palladium acetate, palladium nitrate, palladium oxide, palladium sulfate, sodium tetrachloropalladate (II) and the like.

Usually Pd may be supported on the carrier in an amount of preferably 0.01 to 6% by weight, more preferably 0.1 to 2% by weight based on the weight of the carrier. The use of Pd in an amount of more than 6% by weight is economically inadvantageous.

There is no particular limitation on each of compounds of the metals of the component (c) to be used in preparing the catalyst of the invention. Typical examples of these compounds are halides such as tellurium chloride, selenium chloride, antimony chloride, bismuth chloride and copper chloride, oxides such as tellurium oxide, selenium oxide, antimony oxide, bismuth oxide and copper oxide, nitrates such as bismuth nitrate, copper nitrate, silver nitrate and lead nitrate, acetates such as copper acetate, tin acetate and lead acetate, telluric acid, tellurous acid, selenic acid, selenious acid, antimony sulfide, bismuth sulfide and copper sulfate. Each of the metals may also be used if desired.

Any of substances which are generally used as carriers and which are porous or can be made porous by granulation may be used as carrier substances in the present invention. Examples of the carrier substance are silica, diatomaceous earth, montmorillonite, titania, activated carbon, alumina and silica alumina.

In the process of the present invention for preparing acetic acid by reacting ethylene and oxygen, preferably in the coexistence of water, it is practically advantageous to determine the reaction temperature in the range of preferably 100° to 250° C., more preferably 140° to 200° C. Moreover, it is practically advantageous to determine the reaction pressure from the standpoint of the equipments in the range of normal pressure to 30 kg/cm$^2$G., more preferably in the range of 1 to 15 kg/cm$^2$G.

The gases to be fed to the reaction system in the process of the present invention comprises ethylene, oxygen and steam, and if necessary nitrogen, carbon dioxide or a rare gas may be used as a diluent.

The following amounts of gases are fed to the reaction system, based on the total amount of the fed gases: ethylene: preferably 5 to 80% by volume, more preferably 10 to 50% by volume; oxygen: preferably 1 to 15% by volume, more preferably 3 to 10% by volume; and steam: preferably 1 to 50% by volume, more preferably 5 to 30% by volume.

In carrying out the process of the present invention, it is advantageous to use ethylene of high purity as a starting material. However, ethylene may be mixed with a small amount of lower saturated hydrocarbon such as methane, ethane and propane. Moreover, oxygen diluted with an inert gas such as nitrogen and carbon dioxide, for example, in the form of air, may be fed. However, in the case of recycling the reaction gas, it is generally advantageous to use oxygen at high concentration, most suitably at least at 99%.

Furthermore, the presence of steam is indispensable to the reaction of the invention, and is extremely advantageous to enhance the acetic acid-formation activity and acetic acid-selectivity.

The reaction mixture gas is preferably passed through the catalyst at a space velocity (SV) of 100 to 10,000 Hr$^{-1}$, particularly preferably 300 to 5,000 Hr$^{-1}$ in the standard state.

Examples of the reaction system are a fixed bed system, a fluidized bed system, and the like. However, it is advantageous from the practical standpoint to adopt a fixed bed having corrosion-resistant reaction tubes filled with such a catalyst as described above.

EXAMPLES

The present invention is more concretely illustrated below with reference to examples.

Example 1

In an aqueous solution containing 10 g of sodium tetrachloropalladate (II) was placed 250 ml of a silica carrier having a particle size of 5 mm to absorb the entire solution. The resultant carrier was added to 200 ml of an aqueous solution containing 18 g of sodium metasilicate, and allowed to stand still for 20 hours. Thereafter, 10 ml of 85% aqueous hydrazine was added to the mixture to reduce sodium tetrachloropalladate (II) to metal Pd, and the resultant carrier was washed with water and dried at 110° C. for 4 hours. The carrier containing metal Pd was placed in 90 ml of an aqueous solution containing silicotungstic acid in an amount of 20% by weight based on the weight of the carrier to absorb the entire solution, and dried at 110° C. for 4 hours.

The resultant catalyst in an amount of 15 ml was filled into a reaction tube, and a mixed of gas of ethylene, oxygen, steam and nitrogen in a volume ratio of 50:7:30:13 was introduced thereinto at a temperature of 150° C. and a pressure of 5 kg/cm$^2$ G at a flow rate of 45 Nl/hr to effect reaction. The resultant gas was cooled, and the condensed liquid thus collected was analyzed by gas chromatography.

As a result, the following data were obtained: acetic acid space time yield of 93.1 g/l.hr, acetic acid-selectivity of 78.5%, and $CO_2$ selectivity of 14.2%.

Example 2

The procedure of Example 1 was repeated except that phosphotungstic acid was used in place of silicotungstic acid.

Example 3

The procedure of Example 1 was repeated except that tungstomolybdosilicic acid was used in place of silicotungstic acid.

Example 4

The procedure of Example 1 was repeated except that tungstomolybdophosphoric acid was used in place of silicotungstic acid.

Example 5

The procedure of Example 1 was repeated except that molybdovanadosilisic acid was used in place of silicotungstic acid.

Example 6

The procedure of Example 1 was repeated except that molybdophosphoric acid was used in place of silicotungstic acid.

Example 7

The procedure of Example 1 was repeated except that Ga salt of silicotungstic acid was used in place of silicotungstic acid.

Ga salt of silicotungstic acid was prepared by adding dropwise an aqueous solution containing 0.045 g of gallium nitrate to an aqueous solution containing 9.6 g of silicotungstic acid with stirring.

Example 8

The procedure of Example 7 was repeated except that Mg salt of silicotungstic acid was used in place of Ga salt of silicotungstic acid.

Example 9

The procedure of Example 7 was repeated except that Ga salt of phosphotungstic acid was used in place of Ga salt of silicotungstic acid.

Example 10

The procedure of Example 7 was repeated except that Li salt of silicotungstic acid was used in place of Ga salt of silicotungstic acid.

Example 11

The procedure of Example 7 was repeated except that Cu salt of silicotungstic acid was used in place of Ga salt of silicotungstic acid.

Example 12

The procedure of Example 1 was repeated except that titania was used in place of the silica carrier.

Example 13

In 75 cc of deionized water was dissolved 150 g of phosphotungstic acid. To the solution, a solution of 25 g of cesium nitrate in 160 cc of deionized water was added dropwise. Water in the resulting precipitate was evaporated on a water bath to obtain a clay-like material. The clay-like material was added with a solution of 11.7 g of palladium acetate in acetone, the solvent was evaporated, and then the residue was dried in air at 150° C. for 3 hours. The dried residue was ground to particles of a diameter of 1 to 2 mm, heat treated in air at 200° C. for 3 hours, and then subjected to reduction treatment in hydrogen atmosphere at 250° C. for 5 hours. The catalyst thus obtained was used in the reaction. Procedures other than those described above were carried out in the same manner as described in Example 1.

Comparative Example 1

In an aqueous solution containing 10 g of sodium tetrachloropalladate (II) was immersed 250 ml of a silica carrier having a particle size of 5 mm to absorb the entire solution. The resultant carrier was placed in 200 ml of an aqueous solution containing 18 g of sodium metasilicate, and allowed to stand still for 20 hours. Thereafter, 10 ml of 85% aqueous hydrazine was added to the mixture to reduce sodium tetrachloropalladate (II) to metal Pd. The carrier was then thoroughly washed with water, and dried at 110° C. for 4 hours. The catalyst thus obtained was used in the reaction. Procedures other than those described above were carried out in the same manner as in Example 1.

Comparative Example 2

In 90 ml of an aqueous solution containing silicotungstic acid in an amount of 20% by weight based on the weight of a carrier to be used was immersed 250 ml of a silica carrier having a particle size of 5 mm to absorb the entire solution and dried at 110° C. for 4 hours. The catalyst thus obtained was used in the reaction. Procedures other than those described above were carried out in the same manner as in Example 1.

Comparative Example 3

An acetone solution containing 1.2 g of palladium acetate was added to an aqueous solution containing molybdovanadophosphoric acid in an amount of 20% by weight based on the weight of a carrier to be used. In the resultant solution was immersed 250 ml of a silica carrier having a particle size of 5 mm to absorb the entire solution, and dried at 110° C. for 4 hours. The resultant carrier was further heat treated in air at 320° C. for 5 hours. The catalyst thus obtained was used in the reaction. Procedures other than those described above were carried out in the same manner as in Example 1.

The results thus obtained in Examples 1 to 13 and in Comparative Examples 1 to 3 are shown in Table 1.

TABLE 1

| | Heteropoly-acid | Carrier | Space time yield of acetic acid (g/l · hr) | selectivity (%) | | |
|---|---|---|---|---|---|---|
| | | | | AcOH* | AcH** | $CO_2$ |
| Ex. 1 | silicotungstic acid | silica | 93.1 | 78.5 | 5.5 | 14.2 |
| Ex. 2 | phosphotungstic acid | silica | 83.3 | 78.0 | 5.0 | 16.0 |
| Ex. 3 | tungstomolybdosilicic acid | silica | 91.2 | 77.6 | 4.4 | 17.5 |
| Ex. 4 | tungstomolybdophosphoric acid | silica | 75.1 | 76.5 | 4.1 | 19.2 |
| Ex. 5 | molybdovanadosilisic acid | silica | 94.0 | 61.4 | 19.4 | 17.6 |
| Ex. 6 | molybdophosphoric acid | silica | 68.5 | 77.5 | 4.6 | 17.8 |
| Ex. 7 | Ga salt of silicotungstic acid | silica | 90.4 | 80.1 | 4.1 | 15.6 |
| Ex. 8 | Mg salt of silicotungstic acid | silica | 90.8 | 79.7 | 5.5 | 14.6 |
| Ex. 9 | Ga salt of phosphotungstic acid | silica | 75.6 | 74.8 | 3.2 | 21.8 |
| Ex. 10 | Li salt of silicotungstic acid | silica | 91.0 | 79.9 | 3.9 | 16.1 |
| Ex. 11 | Cu salt of silicotungstic acid | silica | 90.9 | 78.6 | 4.9 | 16.4 |
| Ex. 12 | silicotungstic acid | titania | 91.5 | 79.1 | 4.8 | 14.2 |
| Ex. 13 | Co salt of phosphotungstic acid | none | 41.0 | 77.0 | 5.3 | 17.6 |
| Comp. Ex. 1 | metal Pd only | silica | 0 | 0 | 0 | 100 |
| Comp. Ex. 2 | silicotungstic acid only | silica | 0 | 0 | 0 | 0 |
| Comp. | Pd salt of molybdovanado- | silica | 13.1 | 32.0 | 50.1 | 15.4 |

TABLE 1-continued

| | Heteropoly-acid | Carrier | Space time yield of acetic acid (g/l · hr) | selectivity (%) | | |
|---|---|---|---|---|---|---|
| | | | | AcOH* | AcH** | CO$_2$ |
| Ex. 3 | phosphoric acid | | | | | |

*AcOH = acetic acid
**AcH = acetaldehyde

Example 14

In an aqueous solution containing 10 g of sodium tetrachloropalladate (II) was placed 250 ml of a silica carrier having a particle size of 5 mm to absorb the entire solution. The resultant carrier was added to 200 ml of an aqueous solution containing 18 g of sodium metasilicate, and allowed to stand still for 20 hours. Thereafter, 20 ml of 85% aqueous hydrazine was added to the mixture to reduce sodium tetrachloropalladate (II) to metal palladium, and the resultant carrier was washed with water and dried at 110° C. for 4 hours. The carrier containing metal Pd was placed in 90 ml of an aqueous solution containing 0.43 g of potassium tellurite to absorb the entire solution, and dried at 110° C. for 4 hours. Thereafter, the carrier containing metal Pd and Te was placed in 90 ml of an aqueous solution containing silicotungstic acid (H$_4$SiW$_{12}$O$_{40}$) in an amount of 30% by weight based on the weight of the carrier to absorb the entire solution, and dried at 110° C. for 4 hours.

The resultant catalyst in an amount of 15 ml was filled into a reaction tube, and a mixture gas of ethylene, oxygen, steam and nitrogen in a volume ratio of 50:6:30:14 was introduced thereinto at a temperature of 150° C. and a pressure of 8 kg/cm$^2$ G at a flow rate of 45 Nl/hr to effect reaction.

The resultant gas was cooled, and the condensed liquid thus collected was analyzed by gas chromatography.

As a result, the following data were obtained: acetic acid space time yield of 200 g/l.hr, acetic acid selectivity of 85.5%, and CO$_2$ selectivity of 5.2%.

Example 15

The procedure of Example 14 was repeated except that potassium tellurite was used in an amount of 0.86 g.

Example 16

The procedure of Example 15 was repeated except that phosphotungstic acid (H$_3$PW$_{12}$O$_{40}$) was used in place of silicotungstic acid.

Example 17

The procedure of Example 15 was repeated except that tungstovanadophosphoric acid (H$_3$PW$_{12}$V$_1$O$_{40}$) was used in place of silicotungstic acid.

Example 18

The procedure of Example 15 was repeated except that molybdovanadosilicic acid (H$_5$SiMo$_{10}$V$_2$O$_{40}$) was used in place of silicotungstic acid, and that the reaction was carried out by introducing a gas mixture of ethylene, oxygen, steam and nitrogen in a volume ratio of 50:7:30:13 at a flow rate of 45 Nl/hr at a pressure of 5 kg/cm$^2$ G.

Example 19

In an aqueous solution containing 10 g of sodium tetrachloropalladate (II) was placed 250 ml of a silica carrier having a particle size of 5 mm to absorb the entire solution. The resultant carrier was added to 200 ml of an aqueous solution containing 18 g of sodium metasilicate, and allowed to stand still for 20 hours. Thereafter, 20 ml of 85% aqueous hydrazine was added to the mixture to reduce sodium tetrachloropalladate (II) to metal Pd, and the resultant carrier was washed with water and dried at 110° C. for 4 hours. The carrier containing metal Pd was placed in 90 ml of an aqueous solution containing 0.45 g of potassium antimonate to absorb the entire solution, and dried at 110° C. for 4 hours. Thereafter, the carrier containing metal Pd and Sb was placed in 90 ml of an aqueous solution containing silicotungstic acid (H$_4$SiW$_{12}$O$_{40}$) in an amount of 30% by weight based on the weight of the carrier to absorb the entire solution, and dried at 110° C. for 4 hours.

The reaction was carried out with the catalyst thus obtained under the same conditions as in Example 14.

Example 20

The procedure of Example 14 was repeated except that an aqueous acetic acid solution containing 0.34 g of bismuth nitrate was used in place of the aqueous solution containing potassium tellurite.

Example 21

In an aqueous solution containing 10 g of sodium tetrachloropalladate (II) was placed 250 ml of a silica carrier having a particle size of 5 mm to absorb the entire solution. The resultant carrier was added to 200 ml of an aqueous solution containing 18 g of sodium metasilicate, and allowed to stand still for 20 hours. Thereafter, 20 ml of 85% aqueous hydrazine was added to the mixture to reduce sodium tetrachloropalladate (II) to metal palladium, and the resultant carrier was washed with water and dried at 110° C. for 4 hours. The carrier containing metal Pd was placed in 90 ml of an aqueous solution containing 0.14 g of potassium selenite to absorb the entire solution, and dried at 110° C. for 4 hours. Thereafter, the carrier containing metal Pd and Se was placed in 90 ml of an aqueous solution containing silicotungstic acid (H$_4$SiW$_{12}$O$_{40}$) in an amount of 30% by weight based on the weight of the carrier to absorb the entire solution, and dried at 110° C. for 4 hours.

The resultant catalyst in an amount of 15 ml was filled into a reaction tube, and a mixture gas of ethylene, oxygen, steam and nitrogen in a volume ratio of 50:5:30:15 was introduced thereinto at a temperature of 160° C. and a pressure of 8 kg/cm$^2$ G at a flow rate of 45 Nl/hr to effect reaction.

The resultant gas was cooled, and the condensed liquid thus collected was analyzed by gas chromatography.

Example 22

In an aqueous solution containing 10 g of sodium tetrachloropalladate (II) was placed 250 ml of a silica carrier having a particle size of 5 mm to absorb the entire solution. The resultant carrier was added to 200 ml of an aqueous solution containing 18 g of sodium metasilicate, and allowed to stand still for 20 hours. Thereafter, 20 ml of 85% aqueous hydrazine was added to the mixture to reduce sodium tetrachloropalladate (II) to metal palladium, and the resultant carrier was washed with water and dried at 110° C. for 4 hours. The carrier containing metal Pd was placed in 90 ml of an aqueous solution containing 0.86 g of potassium tellurite to absorb the entire solution, and dried at 110° C. for 4 hours. Thereafter, the carrier containing metal Pd and Te was placed in 90 ml of an aqueous solution containing Mg salt of silicotungstic acid in an amount of 30% by weight based on the weight of the carrier to absorb the entire solution, and dried at 110° C. for 4 hours.

Mg salt of silicotungstic acid was prepared by dissolving 0.12 g of magnesium nitrate in water, and adding dropwise the resultant solution to an aqueous solution containing 28.8 g of silicotungstic acid with stirring.

The resultant catalyst in an amount of 15 ml was filled into a reaction tube, and a mixture gas of ethylene, oxygen, steam and nitrogen in a volume ratio of 50:6:30:14 was introduced thereinto at a temperature of 160° C. and a pressure of 8 kg/cm$^2$ G at a flow rate of 45 Nl/hr to effect reaction.

The resultant gas was cooled, and the condensed liquid thus collected was analyzed by gas chromatography.

Example 23

The procedure of Example 22 was repeated except that Ga salt of silicotungstic acid was used in place of Mg salt of silicotungstic acid.

Example 24

The procedure of Example 22 was repeated except that Li salt of silicotungstic acid was used in place of Mg salt of silicotungstic acid.

Example 25

The procedure of Example 22 was repeated except that Na salt of silicotungstic acid was used in place of Mg salt of silicotungstic acid.

Example 26

The procedure of Example 22 was repeated except that Cs salt of silicotungstic acid was used in place of Mg salt of silicotungstic acid.

Example 27

The procedure of Example 16 was repeated except that 0.68 g of copper acetate was used in place of potassium tellurite.

Example 28

The procedure of Example 14 was repeated except that an aqueous acetic acid solution containing 0.81 g of tin acetate was used in place of potassium tellurite.

Example 29

The procedure of Example 16 was repeated except that 1.3 g of lead acetate was used in place of potassium tellurite.

Example 30

The procedure of Example 14 was repeated except that 0.58 g of silver nitrate was used in place of potassium tellurite.

Example 31

The procedure of Example 14 was repeated except that titanium oxide was used as a carrier.

Example 32

Into 1N aqueous HCl were dissolved 10 g of sodium tetrachloropalladate (II) and 0.43 g of potassium tellurite, and 250 ml of a silica carrier having a particle size of 5 mm was placed in the resultant solution to absorb the entire solution. The resultant carrier was added to 200 ml of an aqueous solution containing 28 g of sodium metasilicate, and allowed to stand still for 20 hours. Thereafter, 20 ml of 85% aqueous hydrazine was added to the mixture to effect reduction, and the resultant carrier was washed with water and dried at 110° C. for 4 hours. The carrier containing metal Pd and Te was placed in 90 ml of an aqueous solution containing silicotungstic acid in an amount of 30% by weight based on the weight of the carrier to absorb the entire solution, and dried at 110° C. for 4 hours.

The resultant catalyst in an amount of 15 ml was filled into a reaction tube, and a mixture gas of ethylene, oxygen, steam and nitrogen in a volume ratio of 50:6:30:14 was introduced thereinto at a temperature of 150° C. and a pressure of 8 kg/cm$^2$ G at a flow rate of 45 Nl/hr to effect reaction. The resultant gas was cooled, and the condensed liquid thus collected was analyzed by gas chromatography.

The results thus obtained in Examples 14 to 32 are shown in Table 2.

TABLE 2

| | Pd-heteropoly-acid-(c) component system catalyst | | | | | |
| | Heteropoly-acid | Carrier | (c) component (atomic ratio to Pd) | Space time yield of acetic acid (g/l · hr) | Selectivity (%) | | |
| | | | | | AcOH* | AcH** | CO$_2$ |
|---|---|---|---|---|---|---|---|
| Ex. 14 | silicotungstic acid | silica | Te(0.05) | 200 | 85.5 | 8.9 | 5.2 |
| Ex. 15 | silicotungstic acid | silica | Te(0.1) | 160 | 79.5 | 16.1 | 4.2 |
| Ex. 16 | phosphotungstic acid | silica | Te(0.1) | 110 | 83.8 | 10.7 | 5.2 |
| Ex. 17 | tungstovanadophosphoric acid | silica | Te(0.1) | 113 | 78.7 | 16.9 | 4.2 |

TABLE 2-continued

| | Pd-heteropoly-acid-(c) component system catalyst | | | | | | |
|---|---|---|---|---|---|---|---|
| | | | (c) component (atomic ratio to Pd) | Space time yield of acetic acid (g/l · hr) | Selectivity (%) | | |
| | Heteropoly-acid | Carrier | | | AcOH* | AcH** | CO$_2$ |
| Ex. 18 | molybdovanadosilisic acid | silica | Te(0.1) | 129 | 51.6 | 37.7 | 9.9 |
| Ex. 19 | silicotungstic acid | silica | Sb(0.05) | 150 | 80.0 | 9.8 | 10.1 |
| Ex. 20 | silicotungstic acid | silica | Bi(0.02) | 155 | 80.2 | 8.8 | 10.6 |
| Ex. 21 | silicotungstic acid | silica | Se(0.02) | 240 | 86.4 | 8.1 | 5.1 |
| Ex. 22 | Mg salt of silicotungstic acid | silica | Te(0.1) | 151 | 79.4 | 17.0 | 3.4 |
| Ex. 23 | Ga salt of silicotungstic acid | silica | Te(0.1) | 159 | 78.9 | 16.5 | 3.6 |
| Ex. 24 | Li salt of silicotungstic acid | silica | Te(0.1) | 159 | 79.7 | 16.6 | 3.6 |
| Ex. 25 | Na salt of silicotungstic acid | silica | Te(0.1) | 158 | 79.1 | 16.3 | 4.5 |
| Ex. 26 | Cs salt of silicotungstic acid | silica | Te(0.1) | 159 | 78.6 | 16.9 | 4.4 |
| Ex. 27 | phosphotungstic acid | silica | Cu(0.1) | 114 | 78.9 | 5.4 | 15.3 |
| Ex. 28 | silicotungstic acid | silica | Sn(0.1) | 140 | 79.6 | 5.8 | 14.4 |
| Ex. 29 | phosphotungstic acid | silica | Pb(0.1) | 115 | 77.4 | 5.5 | 16.8 |
| Ex. 30 | silicotungstic acid | silica | Ag(0.1) | 132 | 78.4 | 5.9 | 15.0 |
| Ex. 31 | silicotungstic acid | titania | Te(0.05) | 191 | 86.0 | 8.1 | 5.5 |
| Ex. 32 | silicotungstic acid | silica | Te(0.05) | 189 | 86.4 | 8.5 | 4.9 |

*AcOH = acetic acid
**AcH = acetaldehyde

We claim:

1. A process for producing acetic acid comprising reacting ethylene and oxygen in the presence of a catalyst comprising (a) metallic Pd and (b) at least one member selected from the group consisting of heteropoly-acids and their salts.

2. A process according to claim 1, wherein the heteropoly-acids comprise one hetero-atom selected from the group consisting of phosphorus, silicon, boron, aluminum, germanium, titanium, zirconium, cerium, cobalt and chromium, and at least one poly-atom selected from the group consisting of molybdenum, tungsten, vanadium, niobium and tantalum.

3. A process according to claim 2, wherein the heteropoly-acids are selected from the group consisting of silicotungstic acid, phosphotungstic acid, phosphomolybdic acid, silicomolybdic acid, tungstomolybdophosphoric acid, tungstomolybdosilisic acid, tungstovanadophosphoric acid, tungstovanadosilisic acid, molybdovanadosilisic acid, borotungstic acid, boromolybdic acid and tungstomolybdoboric acid.

4. A process according to claim 1, wherein the heteropoly-acid salts are metal or onium salts in which the hydrogen atoms of an acid formed by condensing two or more inorganic oxygen acids are partially or entirely substituted by one or more metal or onium cations.

5. A process according to claim 4, wherein the metals by which the hydrogen atoms of the heteropoly-acids are substituted are selected from the group consisting of the metals of the Groups 1, 2, 11 and 13 of Long-Form Periodic Table.

6. A process according to claim 5, wherein the metals by which the hydrogen atoms of the heteropoly-acids are substituted are selected from the group consisting of lithium, sodium, potassium, cesium, magnesium, barium, copper, gold and galliume.

7. A process according to claim 6, wherein the heteropoly-acid salts are selected from the group consisting of lithium, sodium and copper salts of phosphotungstic acid and lithium, sodium and copper salts of silicotungstic acid.

8. A process according to claim 1, wherein the proportion of the components (a):(b) is 1 g atom: 0.025 to 500 g molecules.

9. A process according to claim 1, wherein the catalyst comprises the components (a) and (b) supported on a carrier.

10. A process according to claim 9, wherein the carrier comprises a porous substance.

11. A process according to claim 10, wherein the porous substance is selected from the group consisting of silica, diatomaceous earth, montmorillonite, titania, activated carbon, alumina and silica alumina.

12. A process according to claim 1, wherein metallic Pd of the component (a) is formed by supporting a palladium salt on a carrier and then subjecting the palladium salt to a reduction treatment.

13. A process according to claim 1, wherein the process comprises reacting ethylene and oxygen in the presence of water.

14. A process according to claim 1, wherein the process comprises reacting the ethylene and oxygen in the presence of a catalyst at a temperature of 100° to 250° C. and under pressure of 0 to 30 kg/cm$^2$G.

15. A process according to claim 1, wherein the process comprises reacting 5 to 80% by volume of ethylene, 1 to 15% by volume of oxygen and 1 to 50% by volume of steam in a gas phase.

16. A process for producing acetic acid comprising reacting ethylene and oxygen in the presence of a catalyst comprising (a) metallic Pd, (b) at least one member selected from the group consisting of heteropoly-acids and their salts and (c) at least one member selected from the group consisting of metallic elements of Groups 11, 14, 15 and 16 of the Long-Form Periodic Table.

17. A process according to claim 16, wherein the component (c) is selected from the group consisting of copper, silver, tin, lead, antimony, bismuth, selenium and tellurium.

18. A process according to claim 16, wherein the metallic element of the component (c) is present as a metal or a compound of the element.

19. A process according to claim 16, wherein the heteropoly-acids comprise one hetero-atom selected from the group consisting of phosphorus, silicon, boron, aluminum, germanium, titanium, zirconium, cerium, cobalt and chromium, and at least one poly-atom selected from the group consisting of molybdenum, tungsten, vanadium, niobium and tantalum.

20. A process according to claim 19, wherein the heteropoly-acids are selected from the group consisting of silicotungstic acid, phosphotungstic acid, phosphomolybdic acid, silicomolybdic acid, tungstomolybdophosphoric acid, tungstomolybdosilisic acid, tungstovanadophosphoric acid, tungstovanadosilisic acid, molybdovanadosilisic acid, boroungstic acid, boromolybdic acid and boromolybdotungstic acid.

21. A process according to claim 16, wherein the heteropoly-acid salts are metal or onium salts in which the hydrogen atoms of an acid formed by condensing two or more inorganic oxygen acids are partially or entirely substituted by one or more metal or onium cations.

22. A process according to claim 21, wherein the metals by which the hydrogen atoms of the heteropoly-acids are substituted are selected from the group consisting of the metals of the Groups 1, 2, 11 and 13 of the Long-Form Periodic Table.

23. A process according to claim 22, wherein the metals by which the hydrogen atoms of the heteropoly-acids are substituted are selected from the group consisting of lithium, sodium, potassium, cesium, magnesium, barium, copper, gold and galliume.

24. A process according to claim 23, wherein the heteropoly-acid salts are selected from the group consisting of lithium, sodium and copper salts of phosphotungstic acid and lithium, sodium and copper salts of silicotungstic acid.

25. A process according to claim 16, wherein the proportion of the components (a):(b):(c) is 1 g atom: 0.025 to 500 g molecules: 0.005 to 10 g atoms.

26. A process according to claim 16, wherein the catalyst comprises three components of (a') metallic Pd, (b') at least one member selected from the group consisting of lithium, sodium and copper salts of phosphotungstic acid and phosphotungstic acid, silicotungstic acid lithium, sodium and copper salts of silicotungstic acid and (c') at least one member selected from the group consisting of bismuth, selenium and tellurium.

27. A process according to claim 16, wherein the catalyst comprises the components (a), (b) and (c) supported on a carrier.

28. A process according to claim 27, wherein the carrier comprises a porous substance.

29. A process according to claim 28, wherein the porous substance is selected from the group consisting of silica, diatomaceous earth, montmorillonite, titania, activated carbon, alumina and silica alumina.

30. A process according to claim 16, wherein metallic Pd of the component (a) is formed by supporting a palladium salt on a carrier and then subjecting the palladium salt to a reduction treatment.

31. A process according to claim 16, wherein the process comprises reacting ethylene and oxygen in the present of water.

32. A process according to claim 16, wherein the process comprises reacting the ethylene and oxygen in the presence of a catalyst at a temperature of 100° to 250° C. and under a pressure of 0 to 30 kg/cm²G.

33. A process according to claim 16, wherein the process comprises reacting 5 to 80% by volume of ethylene, 1 to 15% by volume of oxygen and 1 to 50% volume of steam in a gas phase.

* * * * *